(12) United States Patent
Lash

(10) Patent No.: US 8,457,987 B2
(45) Date of Patent: *Jun. 4, 2013

(54) SATORI INTEGRATED HEALTH AND FINANCIAL BENEFITS SYSTEM AND METHOD

(75) Inventor: Steven Lash, San Diego, CA (US)

(73) Assignee: Satori World Medical, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/550,552

(22) Filed: Jul. 16, 2012

(65) Prior Publication Data

US 2012/0284043 A1  Nov. 8, 2012

Related U.S. Application Data

(63) Continuation of application No. 13/196,790, filed on Aug. 2, 2011, now Pat. No. 8,224,668, which is a continuation-in-part of application No. 12/172,941, filed on Jul. 14, 2008, now Pat. No. 8,160,897.

(51) Int. Cl.
*G06Q 10/00* (2012.01)
*G06Q 50/00* (2012.01)

(52) U.S. Cl.
USPC .................................. 705/2; 705/3

(58) Field of Classification Search
USPC ........................................ 705/2–3
See application file for complete search history.

(56) References Cited

U.S. PATENT DOCUMENTS

2008/0015892 A1* 1/2008 Gowdy et al. ............. 705/2

* cited by examiner

*Primary Examiner* — Lena Najarian
*Assistant Examiner* — Minnah Seoh
(74) *Attorney, Agent, or Firm* — Mintz Levin Cohn Ferris Glovsky and Popeo, P.C.

(57) ABSTRACT

A shared medical savings system and method are provided that allow a patient to participate in the savings generated by selecting to have a medical procedure performed overseas. The system has one or more computing devices, a link that is capable of connecting the one or more computing devices to a medical shared savings unit that is capable of interacting with the computing devices. An employer uses the computing device to elect to participate in a medical savings plan using a Health Reimbursement Account, a patient using the computing device to select an overseas medical procedure that is part of the medical savings plan so that the savings for the overseas medical procedure is divided between the employer and the patient utilizing a medical savings plan.

17 Claims, 4 Drawing Sheets

The Cost of Medical Procedures in Selected Countries
(In U.S. dollars)

| Procedure | Retail Price· | Insurers' Cost· | India·· | Thailand·· | Singapore·· |
|---|---|---|---|---|---|
| Angioplasty | $98,618 | $44,268 | $11,000 | $13,000 | $13,000 |
| Heart bypass | $210,842 | $94,277 | $10,000 | $12,000 | $20,000 |
| Heart-valve replacement | $274,395 | $122,969 | $9,500 | $10,500 | $13,000 |
| Hip replacement | $75,399 | $31,485 | $9,000 | $12,000 | $12,000 |
| Knee replacement | $69,991 | $30,358 | $8,500 | $10,000 | $13,000 |
| Gastric bypass | $82,646 | $47,735 | $11,000 | $15,000 | $15,000 |
| Spinal fusion | $108,127 | $43,576 | $5,500 | $7,000 | $9,000 |
| Mastectomy | $40,832 | $16,833 | $7,500 | $9,000 | $12,400 |

· Retail price and insurers' costs represent the mid-point between low and high ranges.
·· U.S. rates include at least one day of hospitalization; international rates include airfare, hospital and hotel.
Source: National Center for Policy Analysis, Report No. 304, dated November 2007

FIGURE 1

SATORI INTEGRATED HEALTH AND FINANCIAL BENEFITS SYSTEM AND METHOD

CROSS REFERENCE TO RELATED APPLICATIONS

The current application is a continuation of application for U.S. patent application Ser. No. 13/196,790, filed on Aug. 2, 2011 and entitled "Satori Integrated Health & Financial Benefits System And Method," now U.S. Pat. No. 8,224,668, which is a continuation-in-part of U.S. patent application Ser. No. 12/172,941, filed on Jul. 14, 2008 and entitled "Satori Integrated Health & Financial Benefits System And Method," now U.S. Pat. No. 8,160,897. This application is also related to co-pending U.S. patent application Ser. No. 13/448,272, filed Apr. 16, 2012, entitled "Satori Integrated Health & Financial Benefits System and Method" which is a continuation of U.S. patent application Ser. No. 12/172,941, filed on Jul. 14, 2008 and entitled "Satori Integrated Health & Financial Benefits System And Method," now U.S. Pat. No. 8,160,897. All applications to which the current application claims priority are incorporated by reference herein in their entireties.

FIELD

The system and method relate generally to a medical shared savings system.

BACKGROUND

By several measures, health care spending continues to rise at the fastest rate in our history. Annual expenditures for health care in the United States have been rising at an astonishing 2 to 5 times the inflation rate since 2000. These increases translate into excessive and rapidly escalating health insurance costs for businesses, as well as, individuals. Over a 5 year period, employers have experienced double digit increases in health plan premiums and, due to price sensitivity, companies attempt to reduce costs annually by changing their healthcare coverage. This disruption of service flow has a dramatic affect on many insurance companies' margins. As costs continue to surge, employers are now faced with many economic challenges and are either unable to or opt not to absorb the higher medical costs. Employees now must face increases in personal contributions to their health plan while millions of others are left without any health insurance coverage at all simply because many employers cannot afford to provide them with medical benefits. In other instances, employees must make the difficult choice as to which members in the family they can afford to insure. For those employers struggling with escalating premiums, price has now become the key selection criteria over provider network and actual benefits. The employer contribution to the average annual premium for a family of 4 reached $12,100 in 2007 and is projected to increase 60% by 2012.

These extraordinary health care cost increases have severely affected multiple segments of our economy and have had a dramatic impact on the ability of US businesses to compete in world markets. One very recent example was the sale of Chrysler® to Cerberus Capital®. Essentially, Chrysler® was sold for with the assumption of its healthcare liability for retirees which was estimated to total $15.7 billion. What is interesting to note is that Daimler-Benz® bought the company less than a decade ago for $60 billion.

Health care costs have increased since 2000 at a rate that is 4 times faster than wage growth. These increases impact many companies ability to increase their workforce resulting in a decelerated job growth market. These costs also suppress many companies' abilities to increase wages for current workers due to the huge increases in employee total compensation costs which include the health care costs. Furthermore, many businesses find it difficult to provide health coverage for employees, and retirees. Thus, by cutting into a company's operating margin, health care costs are reducing their ability to grow by investing in research, capital spending, product development, and marketing with the end result being an inability to compete effectively in world markets. A perfect example can be found in a recent report published by Starbucks® which confirmed that in the last 12 months, their expenditures on health insurance alone surpassed their total costs for raw materials needed to produce the coffee they sell. As another example, General Motors® spends $1500 in health care costs for every car and truck that is produced. This means that the health care expense is more than the cost for the steel used in their car and truck production.

In addition, the wage earnings of workers has been severely affected by rising insurance costs (and premiums) because, for example, many employers have been forced to pass on these premium increases to their workers. Various experts report that the average employee contribution to company-provided health insurance has increased more than 143% in the last 7 years. Currently, an employee, on average, pays 27% of their health insurance premium. Based on this figure, employees are paying $3500 annually for just the premium which does not include co-pays, deductibles, or any other co-insurance. As a consequence of this, the situation exists where even when an employer offers insurance coverage, many employees opt out of the plan because they cannot afford their share of the contribution. Ironically, here in Southern California, some people cross the border into Mexico and pay cash for their healthcare. Thus, while salaries have increased 15% since 2000, average out-of-pocket healthcare expenses have increased 115%. Furthermore, there has been a dramatic increase in the employee responsibility for the cost of healthcare insurance through higher co-pays, deductibles, and cost sharing percentages of the premium.

The continuously rising health care costs in America have potentially adverse consequences for its citizens. Many Americans report that health care is their number one economic concern and the effects of healthcare on their financial stability are already taking place. The Commonwealth Fund reports that an estimated 77 million Americans age 19 and older (2 in 5 adults) have difficulty paying medical bills and have accrued medical debt. Over two-thirds of these families (with medical problems) have health insurance coverage. In a recent study by Harvard University, investigators found that 50% of all bankruptcy filings were partly the result of medical expenses. Experts have also recently reported that 25% of Americans have experienced housing problems, such as the inability to make rent or mortgage payments, due to medical debt. The Urban Institute has projected continued increases in out-of-pocket (co-pays, deductibles, and employee portion of the healthcare premium) healthcare costs. They estimate that in 2030, out-of-pocket healthcare costs will take 30.3% of after-tax income for older unmarried adults up from 17.3% in 2000. Unfortunately, these trends are more than likely to continue unless both businesses and individuals are presented with real options to accessible and affordable health care choices that can not only relieve costly medical burdens but also provide for real financial protection and stability.

It is widely known that the United States spends more money by a significant multiple on medical care than any other advanced industrialized country in the world. Despite the healthcare spending in this country, quality as measured by life expectancy is not as high as it exists in many other developed countries. According to the World Health Organization (WHO), World Health Statistics, 2006, the United States ranks 26 in Life Expectancy at Birth, for Males. While an age of 75 would appear to be excellent, countries such as Canada, Great Britain, Spain, Italy, Australia, Austria, France, Germany, Greece, Israel, Singapore, and others have a much higher life expectancy. Very surprisingly, Cuba, Costa Rica, Ireland, and Finland are comparable to the United States.

The issue is, if the overall health of the population of the United States is not in line with the dollars that we spend (i.e. the notion that if we are outspending other nations by 4 to 5 times on healthcare) then our healthcare (life expectancy) should be better by some significant factor. Therefore, since this is not the case, then there must be health care being delivered outside of the United States that can be utilized at significantly less costs and have equal or better results. The United States' system of health care is burdened with waste, unnecessary redundancies, litigation, bureaucracy, bloat, and a higher cost (standard) of living than other countries providing comparable quality services. It is clear from this data that there are fundamental, deep rooted problems in the U.S. healthcare system that either cannot or will not be solved easily or in a foreseeable period of time. None of the various 2008 election initiatives address the flaws in the system, other than how to provide healthcare coverage for 47 million uninsured Americans.

Medical Travel/Medical Tourism

Over the last few years, in response to more and more American's either losing healthcare coverage and/or anticipating large medical expenses following a diagnosis, a cottage industry has evolved catering to these individuals, under the banner of Medical Tourism. Medical Tourism or Medical Travel is where healthcare services are sought out and delivered outside of the home country of the patient. In other words, medical travel is the act of traveling to other countries to obtain medical, dental, or surgical care. The term was originally coined by the media as a catch all phrase to describe a rapidly growing industry where people travel to obtain medical care, but spend additional time in the host country recuperating and having leisure time post medical procedure.

A combination of factors have led to an increase in popularity of medical travel; the high cost of healthcare in the United States, the ease and affordability of international travel, significant improvements in technology, physician training, certification of hospitals, internet connection capability that connects the patient overseas with family members at home, and overall quantum improvements in the standard of care in many overseas countries.

According to research by the University of Delaware "The cost of surgery in Bolivia, Argentina, India, Thailand, Colombia, Philippines or South Africa can be one-tenth of what it is in the United States or Western Europe, and sometimes even less. A heart-valve replacement that would cost US$200,000 or more in the U.S., for example, goes for $10,000 in the Philippines and India—and that includes round-trip airfare and a brief vacation package which also includes costs for travel and lodging for a companion. Similarly, a metal-free dental bridge worth $5,500 in the U.S. costs $500 in India or Bolivia and only $200 in the Philippines, a knee replacement in Thailand with six days of Physical Therapy costs about one-fifth of what it would in the States, and Lasik Eye Surgery worth $3,700 in the U.S. is available in many countries for $730. Cosmetic surgery savings are even greater. A full facelift that would cost $20,000 in the U.S. runs about $2,700 in the Philippines or $2,500 in South America or $2,300 in Bolivia." FIG. 1 shows the difference in cost of different medical procedures in the United States (shown as the retail price), India, Thailand, and Singapore.

Thus, it is necessary to provide a patient medical savings sharing system that not only overcomes the problems associated with rising healthcare costs but also takes advantage of the medical travel/medical tourism phenomenon and it is to this end that the system and method are directed.

BRIEF DESCRIPTION OF THE DRAWINGS

FIG. 1 is a chart that compares the cost for a number of medical procedures in selected countries;

DETAILED DESCRIPTION OF ONE OR MORE EMBODIMENTS

The system and method are particularly applicable to the Satori® Integrated Health & Financial Benefits System implemented as shown in the diagrams and it is in this context that the system and method will be described. In one implementation, Satori® Integrated Health & Financial Benefits System may be implemented over the web as will be enabled at www.satoriworldmedical.com, but the system and method are not limited to the implementation of the system as shown at that site. It will be appreciated, however, that the system and method has greater utility since the system and method can be implemented in other manners, with other architectures, etc. that are within the scope of the disclosure.

The system and method for Satori® Integrated Health & Financial Benefits System shares the savings attributable to the patient selecting a necessary medical procedure when the medical/dental procedure is performed outside of the United States. The savings is shared between the health insurer/employer and the patient. Various embodiment of the system are described below that can be used by including but not limited to by self-funded employers, Health Maintenance Organizations (HMO's), Medicare/Medicaid/MediCal organizations, Preferred Provider Organizations (PPO's), pension plans (healthcare liability), municipalities, unions, worker's compensation carriers, and the like.

In the system and method, the savings may be shared with the patient using various different mechanisms. Generally, the savings are shared using a tax-exempt health spending accounts or a tax-exempt welfare benefit plan which are tax free pursuant to Section 105 of the Internal Revenue Code. Examples of these accounts may include a health reimbursement account (HRA), a limited-purpose HRA, a post-deductible HRA, a suspended HRA, a retirement HRA, a flexible savings account (FSA), a limited-purpose FSA, a post-deductible FSA, a medical savings account (MSA), an Archer MSA and the like. The savings may also be shared by direct cash payments.

Figure 2A:
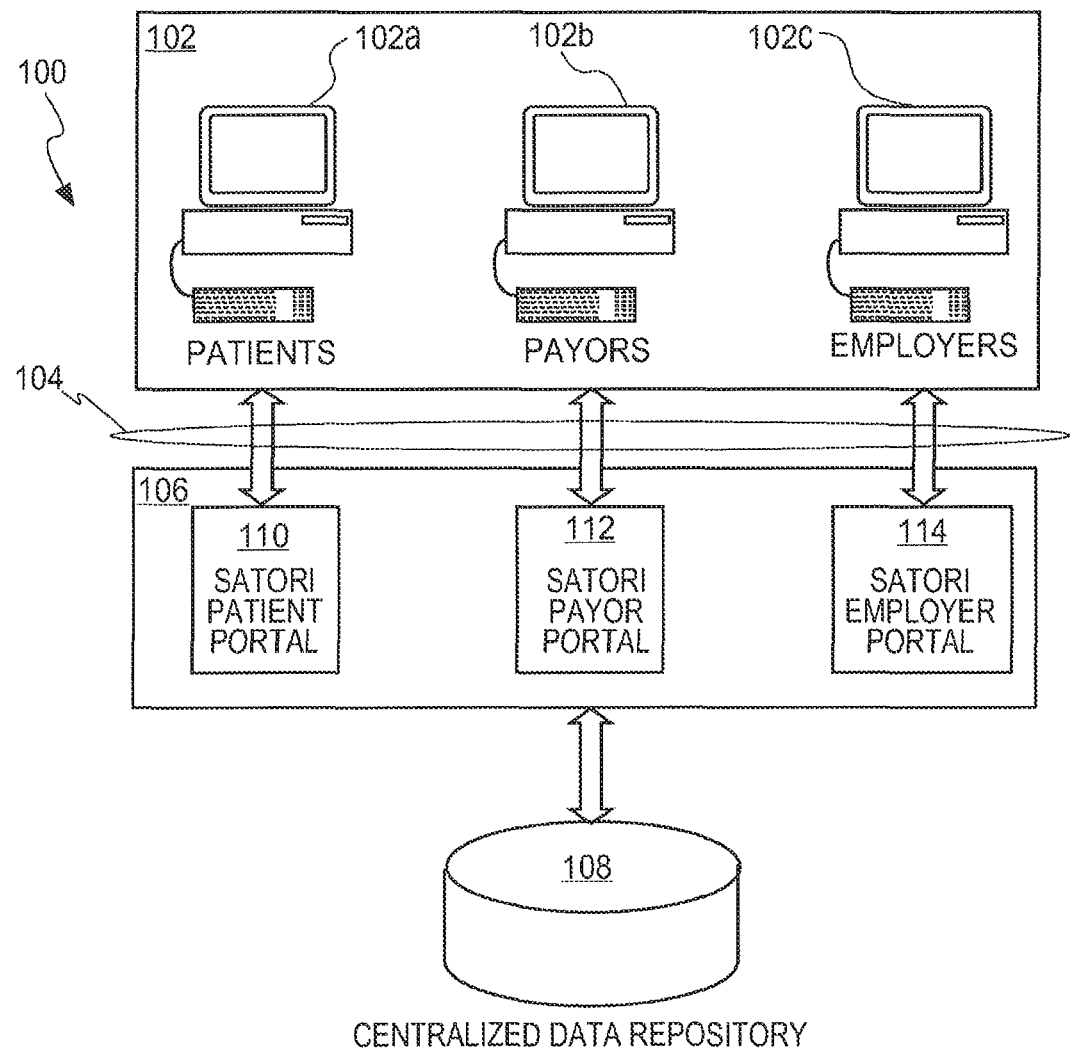
FIG. 2A illustrates a medical shared savings system.

FIG. 2A illustrates the Satori® Integrated Health & Financial Benefits System 100 that includes one or more user computing devices 102, such as one or more patient computing devices 102a, one or more payor computing devices 102b and one or more employer computing devices 103c as shown in FIG. 2A. Each computing device may be a processing unit based device with sufficient memory, display capabilities, and connectivity to interact with a medical expense unit 106. For example, each computing device may be a personal computer, a laptop computer, a tablet computer, a cellular phone, a smart phone, a PDA and the like. Each computing device 102 may be capable of connecting with a link 104 wherein the link may be a computer network, a communications network, a wired network or a wireless network. In one embodiment, the link 104 may be the Internet. The link 104 allows each computing device 102 to interact with the medical expense unit 106. In one embodiment, the medical expense unit 106 may be one or more server computers that allow a connection to the computing devices 102 and serve information and content to the computing devices such as using a web server that serves web pages that are displayed on a browser application that is being executed by a processing unit of each computing device. The medical expense unit 106 and the computing devices 102 may also interact with each other in other manners that are within the scope of the Satori® Integrated Health & Financial Benefits System.

The system may also include a store 108 that stores information associated with the system such as, for example, medical claims data, cost per procedure data, patient data, payor data, employer data, physician data, hospital accreditation data, technical medical procedure data and the like. The patient data may include for each patient, for example, demographics, contact information, diagnosis and procedure data, insurance data, travel itinerary information, and more. The payor data may include, for example, account information, claims data including history, cost for procedure, mortality and morbidity rate, outcomes data, and the like, as well as, subscriber data. The employer data may include, for example, coverage data, hospital data such as inpatient and outpatient facility information, claims history, information systems utilized, physician and nurse data, and the like. The physician data may include, for example, biographies, CVs, licensing and credentials, language capacity, quality data including outcomes, and the like. The hospital data may include accreditation data for example, standards and evaluation methods including assessment and care processes, education, management of information and human resources, quality leadership, infection control, blood handling processes, facility equipment and technology, recording handling, patient privacy, hospital transport services, diagnostic capabilities, patient communication procedures, collaborative integrated management, compliance, and the like. The medical procedure data may include information about various medical procedures, such as for example, cardiac procedures, orthopedic procedures, spine procedures, cancer procedures, vascular procedures, cosmetic procedures, dental procedures, urology procedures, addiction therapy, women's health procedures including fertility, cancer, bariatric surgery, general surgery, stem-cell therapies, neurosurgery, living donor transplants, and others. The store 108 also may include safety data, pricing data, travel data, such air and ground transportation, hotel accommodations, and the like. The store 108 may further include country data, such as capital, location, maps, climate, languages, economic factors, currency, communication, transportation, and the like, and media information such as articles, press releases, and the like. In one implementation, the medical expense unit 106 may further include, as shown in FIG. 2A, a patient portal 110, a payor portal 112 and an employer portal 114 wherein each portal may be one or more server computers that execute computer code to implement the operations of each of the portals.

Figure 2B:
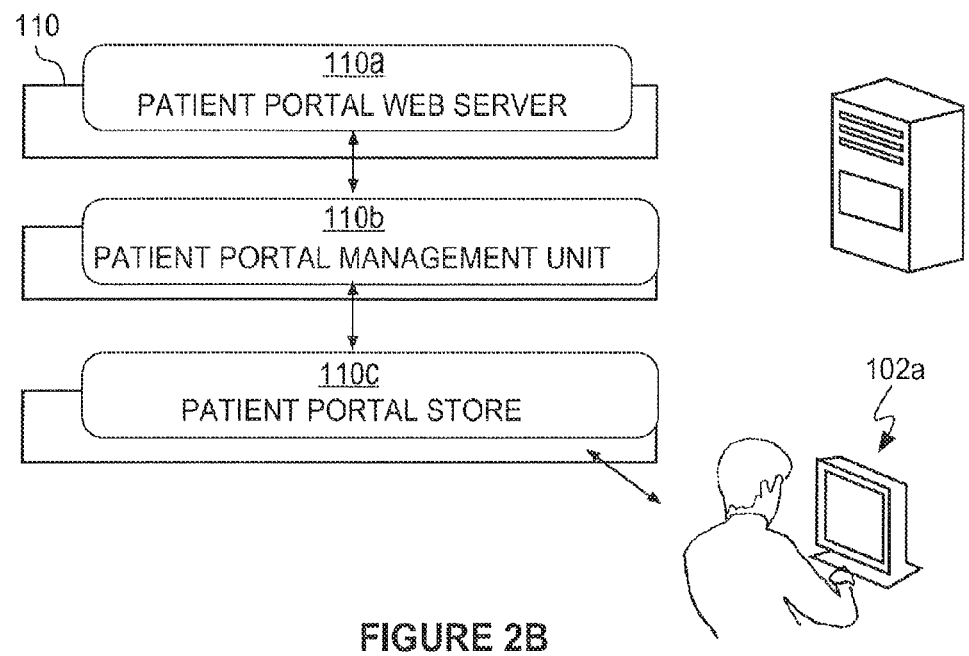
FIG. 2B illustrates more details of the patient portal of the medical shared savings system.

FIG. 2B illustrates more details of an implementation of the patient portal 110. The patient portal may be implemented using one or more server computers that execute computer code as described above. The patient portal may include a patient portal web server 110A (which may be implemented as a software based commercially available web server) that interacts with the one or more patient computing devices 102a (as shown in FIG. 1) to establish TCP/IP connections with these patient computing devices and to exchange data/information with these one or more patient computing devices. In one implementation, the information/data may be exchanged using web pages and forms in web pages. The patient portal may also include a patient portal management unit 110B and a patient portal store 110C wherein the patient portal store stores information associated with the patient portal and the patient portal management unit manages the patient portal store and interacts with the web server as shown. In one implementation, the patient portal management unit is a plurality of lines of computer code being executed by one or more patient portal processing units that are part of the one or more server computers and the store is a software implemented relational database system. Thus, the patient portal 110 may provide a new patient or returning patient (a person who needs to have a medical procedure performed) with information about how to save money with the system, how much can be saved with the system based on their medical/health plan coverage, how to derive an economic benefit with the system, instructions to register for the system, process of utilizing the system, information about medical procedures outside of the United States, information regarding our network of hospitals, physicians, and other affiliates, information on how to use the system, the benefits of utilizing the system, etc.

Figure 2C:
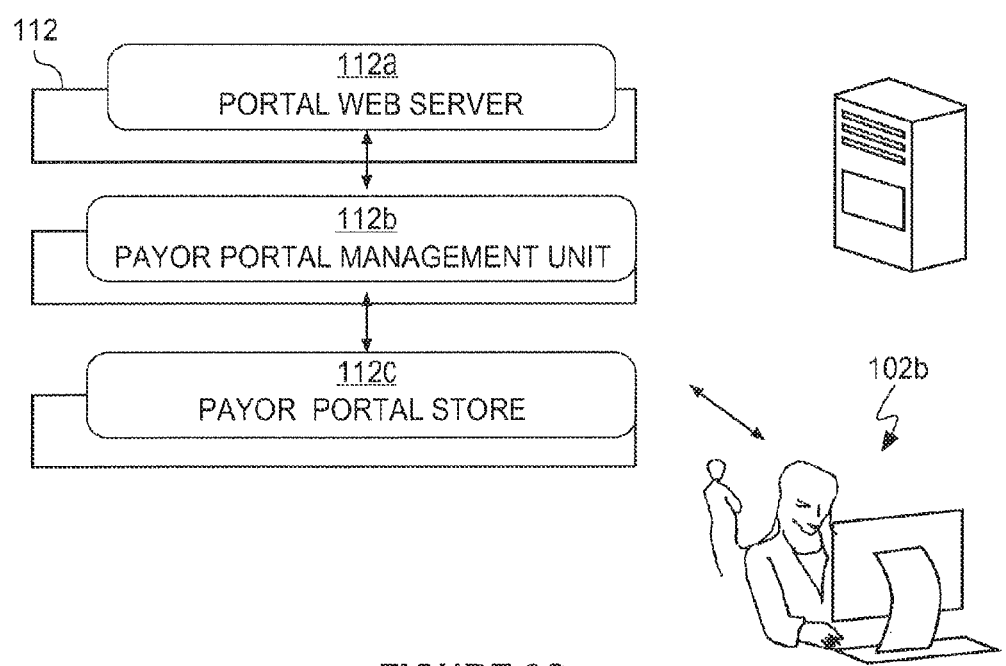
FIG. 2C illustrates more details of the payor portal of the medical shared savings system.

FIG. 2C illustrates more details of an implementation of the payor portal 112. The payor portal may be implemented using one or more server computers that execute computer code as described above. The payor portal may include a payor portal web server 112A (which may be implemented as a software based commercially available web server) that interacts with the one or more payor computing devices 102b (as shown in FIG. 1) to establish TCP/IP connections with these payor computing devices and to exchange data/information with these one or more payor computing devices. In one implementation, the information/data may be exchanged using web pages and forms in web pages. The payor portal may also include a payor portal management unit 112B and a payor portal store 112C wherein the payor portal store stores information associated with the payor portal and the payor portal management unit manages the payor portal store and interacts with the web server as shown. In one implementation, the payor portal management unit is a plurality of lines of computer code being executed by one or more payor portal processing units that are part of the one or more server computers and the store is a software implemented relational database system. Thus, the payor portal 112 may provide a payor (an organization who is going to pay for the medical expense) with information about the system and its operations, registration information, benefits of utilizing the Satori Integrated Health & Financial Benefits System such as the amount of dollars that the organization would save by utilizing the Satori Global Network™. Additionally it would reflect improved operating margin, provider network, competency of network, quality indicators, an increase in payor's marketplace advantage, and the like.

Figure 2D:
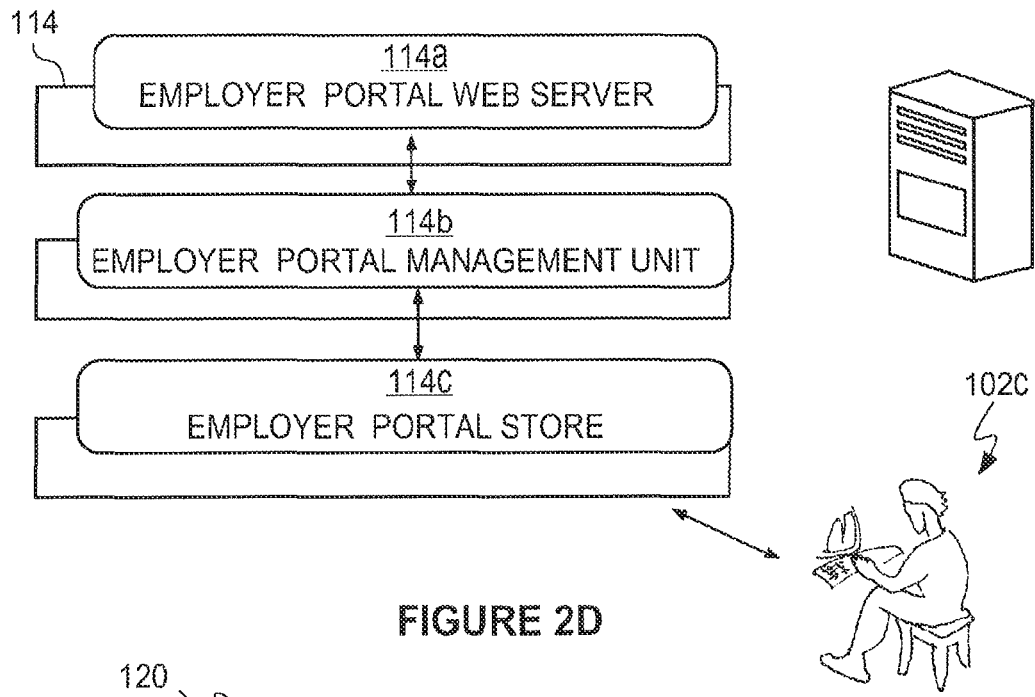
FIG. 2D illustrates more details of the employer portal of the medical shared savings system.

FIG. 2D illustrates more details of an implementation of the employer portal 114. The employer portal may be implemented using one or more server computers that execute computer code as described above. The employer portal may include an employer portal web server 114A (which may be implemented as a software based commercially available web server) that interacts with the one or more employer computing devices 102c (as shown in FIG. 1) to establish TCP/IP connections with these employer computing devices and to exchange data/information with these one or more employer computing devices. In one implementation, the information/data may be exchanged using web pages and forms in web pages. The employer portal may also include an employer portal management unit 114B and an employer portal store 114C wherein the employer portal store stores information associated with the employer portal and the employer portal management unit manages the employer portal store and interacts with the web server as shown. In one implementation, the employer portal management unit is a plurality of lines of computer code being executed by one or more employer portal processing units that are part of the one or more server computers and the store is a software implemented relational database system. Thus, the employer portal 114 may provide the employer (an entity or individual who employs the patient) with information about the system and its operations, registration information and benefits of utilizing the Satori® Integrated Health & Financial Benefits System including a reduction in operational costs. A reduction in operational costs yields an increase in profits which can be applied to additional investment in marketing, expansion, research, capital spending, product development. Another benefit of the system is an increase in employee productivity, retention, and reduction of absenteeism due to the ease of access to affordable procedures through the Satori Global Network™ that eliminates the employee's delay in having medical procedures done due to their personal, large out-of-pocket costs. Through the utilization of the Health Reimbursement Account the employer will be able to give their employees access to high-quality care and still receive 100% of the benefit through the tax deduction even though they will be sharing a percentage of the savings with the employee. Thus, for the first time, by utilizing the savings plan, provides a vehicle for the patient to receive an economic a benefit for choosing a less costly alternative treatment, but receiving high quality care.

Figure 3:
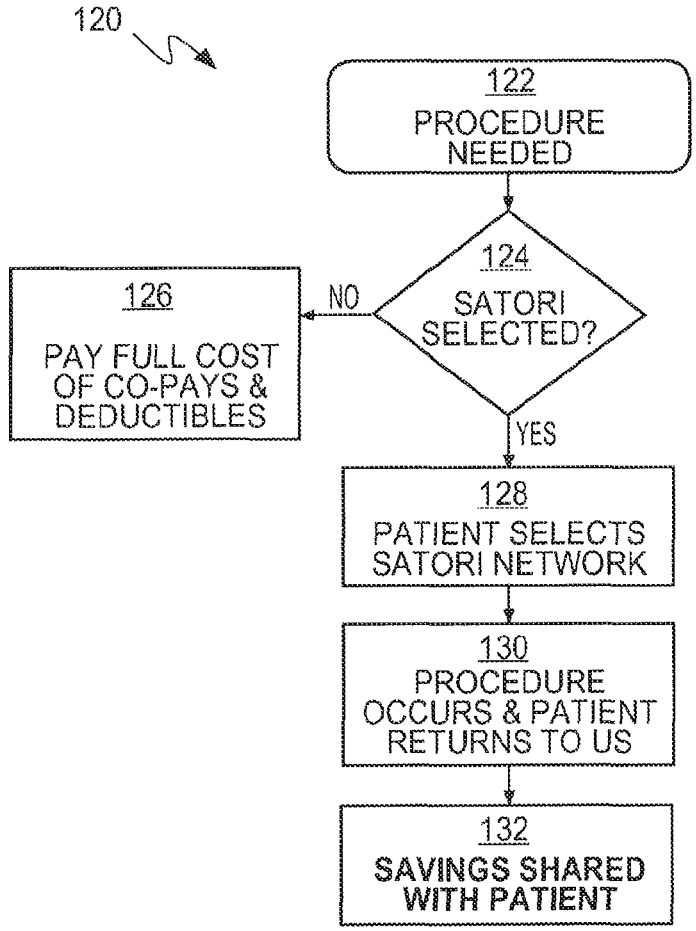
FIG. 3 is a flowchart of a method for the calculation of the dollars that will be saved.

FIG. 3 is a flowchart of a method for the Satori® Integrated Health & Financial Benefits System 120. Following the overall description of the medical shared savings method, particular examples of different employers and how they can use the system and method will be provided. In the method 120, a patient needs a medical procedure (122). The patient then decides whether or not to use the Satori® Integrated Health & Financial Benefits System (124). If the patient does not use the Satori system, he/she pays the full cost with co-pays, co-insurance, and deductibles (126). If the patient elects to use the Satori® system, the patient selects the Satori Global Network™ of hospital and physician providers outside of the United States (128) (an overseas medical procedure not performed in the United States by an overseas medical provider) and the procedures occur outside of the United States and the patient returns to the United States when they have recovered and have been discharged from the care of the overseas physician (130). The non-US performed medical procedure will also include within the surgical procedure costs, all necessary post-operative medical follow-up care delivered outside the United States, e.g. Physical Therapy. In addition, due to the uniqueness of the model utilizing a Health Reimbursement Account, ongoing prescription, medical premium, and other expenses are paid for by the savings generated by having the procedure done internationally, by the system. The savings due to the medical procedure being performed outside of the United States (See FIG. 1 for an example of the cost differences between a US procedure and the same procedure in other foreign countries) is then shared with the patient (132) so that the employer, payor, and patient all receive some economic benefit (share the savings) from the medical procedure being performed outside of the United States.

The Satori® Integrated Health & Financial Benefits System includes interactive capabilities which allow users to interface with our database(s) in a number of different ways. The patient user menu is comprised of categories which include various medical procedures; US retail pricing, employer/financial sponsor costs, insurer costs, patient costs such as deductibles, co-pays, co-insurance, premiums, and more. The user is able to input personal information such as their selected procedure, employer/financial sponsor, health insurance carrier and their particular benefit plan, surgery destination country, and more, as well as, utilize drop down menus to analyze procedure costs, savings, and direct economic benefit. Once the information is entered and submitted, the software system then calculates the user's savings when selecting the Satori Global Network™ verses that of the US healthcare system, as well as, computes the actual financial benefit they will receive from the shared savings which will also include dollars saved from deductibles, co-pays, and co-insurances not being charged to the patient by utilizing the Satori Global Network™. The system displays the real dollar benefit received from their employer/financial sponsor due to the savings and upon the completion of the overseas surgical procedure the share of the savings are then deposited it into their employee's Health Reimbursement Account.

The employer/financial sponsor user menu is comprised of categories which include procedures; US retail pricing, employer/financial sponsor costs, insurer costs, patient costs such as deductibles, co-pays, co-insurance, premiums, and more. The user is able to input company information such as company size, demographics, employee personnel profiles, procedures, medical claims data including historical costs, health insurance carriers and benefit plans, premiums for employees and dependents, surgery destinations, and more, as well as, utilize drop down menus to analyze procedure costs and savings. Once the information is entered and submitted, the software system then calculates the user's savings when the employee selects the Satori Global Network™ verses that of the US healthcare system. The software system will calculate the real dollar financial benefit they will receive, as well as, calculate the shared portion that they will need to deposit into their employee's Health Reimbursement Account.

The insurer user menu is comprised of categories which include procedures; US retail pricing, employer/financial sponsor costs, insurer costs, patient costs such as deductibles, co-pays, co-insurance, premiums, and more. The user is able to input company information such as type of carrier, member/company, procedures, benefit plans, revenue received from members, surgery destinations, and more, as well as, utilize drop down menus to analyze procedure costs and savings. Once the information is entered and submitted, the software system then calculates the user's savings when the member selects the Satori Global Network™ verses that of the US healthcare system. The software system will calculate the real dollar financial benefit they will receive.

As a result of the method shown in FIG. 3, the patient benefit includes no deductibles and no co-pays as described below in more detail. Alternatively, the patient benefit may be a 100% medical benefit meaning that the patient is covered for all of the costs for the overseas medical procedure including the deductibles and co-pays.

Health Reimbursement Account Embodiment

In one embodiment, the system may use a Health Reimbursement Account. Health Reimbursement Accounts or "personal care accounts," are a type of health insurance plan that reimburses employees for qualified medical expenses. The U.S. Department of the Treasury issued guidance on health reimbursement accounts in a revenue ruling in June 2002.

Health Reimbursement Accounts consist of funds set aside by employers to reimburse employees for qualified medical expenses, just as an insurance plan will reimburse covered individuals for the cost of services incurred. The guidance provided by the Department of the Treasury makes it clear that Health Reimbursement Accounts are not a new type of account designated within the Internal Revenue Code. Rather, employers qualify for preferential tax treatment of funds placed in a Health Reimbursement Account in the same way that they qualify for tax advantages by funding an insurance plan because employers can deduct the cost of an insurance plan—and now a Health Reimbursement Account—as a business expense under Internal Revenue Code section 162.

Health Reimbursement Accounts are open to employees of companies of all sizes. A Health Reimbursement Account provides "first-dollar" medical coverage until funds are exhausted. For example, if an employee has a $500 qualifying medical expense, then the full amount will be covered by the Health Reimbursement Account if the funds are available in the account. Under a Health Reimbursement Account, the employer provides the funds, not the employee. All unused funds are rolled over at the end of the year. Former employees, including retirees, can have continued access to unused reimbursement amounts if the employer allows this. Health Reimbursement Accounts remain with the originating employer and do not follow an employee to new employment, thereby providing an incentive for the employee not to change jobs.

Using the Satori® Integrated Health & Financial Benefits System described above, an employee, member, subscriber or a potential patient decides to seek care utilizing the Satori Global Network™. Since the medical care is at a substantial savings compared to traditional US medical care, real dollar savings are generated for the paying entity (e.g., an employer), as well as, the individual patient. Under the Satori model, for example the employer/sponsor keeps 75% of the savings (or any other percentage that the payor/sponsor chooses) and the patient receives (via a Health Reimbursement Account), 25% (or the difference between what the payor keeps and 100%) of the savings for which he or she is free to use for permitted health expenses under the Internal Revenue Code. The savings can also be a fixed dollar amount. This significant process improvement allows for both lowering an organization's health care costs, as well as, lowering of the patient's health care cost, which, through this method, is tax free to the patient. It has the potential to allow workers to pay for their healthcare premiums for several years along with any future co-pays, deductibles, and other co-insurance for other necessary medical care required. Overall, this process improvement provides for high quality medical care, lower healthcare costs for the business or sponsoring entity and a tax free health care fund that provides first dollar coverage, including premium payments for the employee/member/subscriber or patient with the potential to do so for several years.

The organizations that can benefit through this process (as the employer or payor) are: employers—large and small, unions, workers compensation carriers, pension plans/funds, employers that self fund their health care expense, Taft-Hartley Trust, Third Party Administrators (TPAs), Health Maintenance Organizations (HMOs) and/or Preferred Provider Organizations (PPOs). An example of how the system and method works for each type of payor/employer is now provided.

Self-Funded Employers

Self funded companies directly retain the risk for medical expenses since they do not offload that risk to an insurer (Although they may purchase reinsurance for catastrophic claims.) The self funded companies typically utilize a TPA (Third Party Administrator) to be the administrative and medical management arm of their health offering. Typically, the TPA provides a network of contracted hospitals, physicians and ancillary care providers; adjudicates and pays claims; processes enrollments and disenrollments; and performs an array of utilization management functions such as large case management and disease management. The self funded employers typically represent about ⅓ of the employers with medical coverage in a community and represent 500 or more covered lives. The Satori® Integrated Health & Financial Benefits System and method would utilize a shared savings plan between employers and employees through a Health Reimbursement Account (HRA) mechanism or other embodiments of sharing savings plans.

Health Maintenance Organizations

HMOs are regulated by state authorities. HMOs generally must file changes to their benefit plans with state regulators who have the power to approve or challenge them. Regulators typically look favorably on benefit changes giving members additional choices and/or reduced cost (such as that provided by the Satori® Integrated Health & Financial Benefits System is and method described above.)

If a HMO participant were to sign up for the Satori Global Network™ as part of their HMO offering, we would, in concert with the HMO's legal department, craft incentives that would be consistent with state law and the HMO's approved benefit structure. There are several ways that these incentives could be crafted to include: 1) reduced premium for the company and employee making the Satori selection; 2) the HMO provides a premium rebate (or credit on future billings) to an employer for an employee utilizing the Satori service (after the procedure is performed) and then a comparable incentive plan for the employee could be implemented using a HRA; 3) co-payments and deductibles would be waived for procedure; and/or 4) 100% coverage with no out-of-pocket costs.

Preferred Provider Organizations

There are different incentives depending if the Satori® Integrated Health & Financial Benefits System is linked to an insured PPO or a PPO that simply offers provider networks for rent. In either case, the Satori® system would be a network provider, just like any other organization, and if a member/company selected Satori® for their network, the incentives could work in the same manner as an HMO as described above. If the medical shared savings system is part of a provider network PPO which bills the underwritten entity (an insurer or self funded employer), the incentives are easier to implement because the underwriter controls the benefits and structure; Satori® would simply be part of a "rent a network" structure, and therefore the method would be implemented using a Health Reimbursement Account.

Pension Plan (Healthcare Liability)

As these dollars are controlled via trust or defined plan, the medical shared savings incentives would need to be crafted consistent with the terms of the trust. These individuals are retirees (not yet Medicare eligible) and are not considered employees so a HRA is not available for use since the HRA is funded exclusively by the employer. However, there is the potential that the employer would establish the HRA as part of its structure in advance of a healthcare retiree becoming eligible for this coverage and therefore the embodiment using a HRA is available. A Medical Savings Account could, however, be established for any individual that would allow for payments of future healthcare expense wherein deposits could be made by sponsoring organization based on savings from utilizing the medical shared savings system. In addition, other incentives can be implemented in lieu of a Medical Savings Account if the Satori® Integrated Health & Financial Benefits System is used, such as no co-pays, no deductibles, and/or waiver of future premium contributions by recipient.

Municipalities

Some states (Colorado and Virginia) have introduced legislation permitting state employees to go outside the United States for health care. Furthermore, cities have a significant funding crisis for its retiree (too young to be Medicare eligible) healthcare liability and each one has a different program based on its own plan design. The Satori® Integrated Health & Financial Benefits System will provide a no out-of-pocket-cost incentive program for recipients so that anytime a plan participant selects the Satori® system, the recipient would have significantly reduced healthcare expenses going forward for several years.

Unions

Unions control the funding and benefit design of their trusts plans which creates a flexible environment for medical shared savings system incentives. For example, the savings generated from a member utilizing the Satori® Integrated Health & Financial Benefits System could be utilized to fund additional benefits, for example dental coverage, vision coverage or prescription drug coverage. If the Satori® system was used, incentives could include significantly reduced future premium funding by the member for several years, and/or waive co-payments, deductibles, and other co-insurance.

As shown above, regardless of the type of payer, the sponsoring organizations would understand that in order to utilize the Satori® Integrated Health & Financial Benefits System, they are required to share the savings with the member/recipient/beneficiary/patient. Whatever benefit the patient gets, the underwriter/sponsoring organization will get threefold or more; so there is no downside for including the Satori Global Network™ option. Since any contribution to a Health Reimbursement Account is tax deductible to the sponsor they still receive 100% of the savings, while creating a novel economic incentive for the individual to choose Satori.

Satori's shared savings model will provide the opportunity to make real and significant changes in the delivery of health care services to Americans. The unique and innovative approach empowers consumers, employers, and payors of health care services with the ability to make choices that will provide them with a direct tangible financial benefit. In this model, the consumer is at the center point of the decision process, but all the stakeholders will win by the consumer selecting the Satori Global Network™. For the first time ever, a medical shared savings system will provide real solutions to some of our biggest health care problems by aligning high quality and economic benefit for all the stakeholders. Businesses will utilize the system to reduce operational expenses and thus be given the financial opportunity to invest in employee retention, market expansion, market research, capital spending, product development, and marketing and also still have 100% of the savings. Additionally, businesses will be given more control over health care expenditures. Employees will, for the first time ever, receive a direct and tangible economic benefit from choosing the Satori Global Network™ option. Instead of being forced to make dramatic lifestyle changes, such as filing bankruptcy or foreclosing, due to the accrual of medical debt or not seeking medical care due to the high co-pay and deductibles, individuals now can avoid all of this with the protective financial blanket provided by the Satori Integrated Health & Financial Benefits System. The savings will be passed on directly to the consumer in a number of ways. Deductibles, co-pays, co-insurance portions will be waived. A portion of the savings between the costs of procedures in the US verses those in the Satori Global Network™ can be placed in a HRA, which is tax-free to the individual, and those deposited funds can be utilized to pay future premiums and other costs incurred by the subscriber which may last for several years. In essence, the Satori Integrated Health & Financial Benefits System and this method will provide individuals with economic security. Payors will also benefit through the opportunity to dramatically reduce their expenditures by offering their subscribers the Satori Global Network™ option. The Satori model is likely to reduce their customers need to change plans, thus saving them from excessive product development and delivery costs.

The Satori® Integrated Health & Financial Benefits System will be advantageous to all parties involved. This revolutionary model clearly will meet the demands of today's marketplace. By including the Satori® system and comparing its costs, benefits, and outcomes against those of US healthcare providers, those who pay the bills will have an important new tool for performance measurement. In essence, the Satori® system's value is in applying downward price pressure on the medical industry that has heretofore been isolated from the international pressures faced by virtually all other facets of the American economy. The Satori® Integrated Health & Financial Benefits System offers an immediate, tangible method for reducing the significant outlays associated with the high cost procedures that will be increasingly required by aging Baby Boomers.

While the foregoing has been with reference to a particular embodiment of the invention, it will be appreciated by those skilled in the art that changes in this embodiment may be made without departing from the principles and spirit of the invention, the scope of which is defined by the appended claims.

The invention claimed is:

1. A medical shared savings system, comprising:
   a data store that stores medical plan information for a medical plan associated with a patient, and that stores pricing data for a medical procedure under a medical savings plan, the pricing data including a cost of the medical procedure offered in the United States according to the medical plan and a cost of the medical procedure offered in one or more regions outside of the United States, the pricing data including travel costs; and
   a medical shared savings unit that interacts with one or more computing devices and the data store via a communications network, the medical shared savings unit receiving a selection from one of the one or more computing devices to select the medical procedure as part of the medical savings plan, and calculating a savings based on a difference between the cost of the medical procedure performed in a patient-selected region outside of the United States and the cost of the medical procedure performed within the United States, the medical shared savings unit dividing the savings based on a medical savings plan model when the patient undergoes the medical procedure in the patient-selected region outside of the United States, the medical savings plan model designating less than half of the savings for the patient using one of a tax-exempt account and a direct cash payment to the patient.

2. The medical shared savings system in accordance with claim 1, wherein the medical shared savings unit further divides the savings with the patient based on the medical savings plan model.

3. The medical shared savings system in accordance with claim 1, wherein the pricing data includes costs for post-operative services related to the medical procedure.

4. The medical shared savings system in accordance with claim 1, wherein the pricing data includes costs for ongoing prescriptions related to the medical procedure.

5. The medical shared savings system in accordance with claim 1, wherein the one or more computing devices includes a payor computing device associated with a payor of the medical plan and of the savings.

6. The medical shared savings system in accordance with claim 1, wherein the one or more computing devices includes a patient computing device associated with the patient, and configured to receive and transmit the selection to the medical shared savings unit.

7. A computer-implemented method comprising:
storing, in a data store, medical plan information for a medical plan associated with a patient, the medical plan information including pricing data for a medical procedure for each of a plurality of medical providers in a medical plan network associated with the medical plan, the plurality of medical providers including at least one medical provider in a region outside of the United States, the pricing data including travel costs;
receiving, by a computer via a communications network, a selection from a computing device to select one of the at least one medical provider in the region outside of the United States for the patient as part of a medical savings plan associated with the medical plan;
accessing, by the computer, the medical plan information from the data store;
calculating, by the computer, a savings based on a difference between a cost of the medical procedure performed in the patient-selected region outside of the United States and a cost of the medical procedure performed within the United States;
dividing, by the computer, the savings at an unequal percentage when the patient undergoes the medical procedure in the patient-selected region outside of the United States; and
designating a smaller portion of the divided savings for the patient using one of a tax-exempt account and a direct cash payment to the patient.

8. The computer-implemented method in accordance with claim 7, wherein the computing device is one of a mobile device or computer.

9. The computer-implemented method in accordance with claim 7, wherein the computing device is operated by the patient.

10. The computer-implemented method in accordance with claim 7, wherein the pricing data includes costs for post-operative services related to the medical procedure.

11. The computer-implemented method in accordance with claim 7, wherein the pricing data includes costs for ongoing prescriptions related to the medical procedure.

12. A computer-implemented system, comprising:
a data store that stores medical plan information for a medical plan associated with a patient, and that stores pricing data for a medical procedure under a medical savings plan, the pricing data including a cost of the medical procedure offered in the United States according to the medical plan and a cost of the medical procedure offered in one or more regions outside of the United States, the pricing data including travel costs; and
a medical shared savings unit that interacts with one or more computing devices and the data store via a communications network, the medical shared savings unit receiving a selection from one of the one or more computing devices to select the medical procedure as part of the medical savings plan, and calculating a savings based on a difference between the cost of the medical procedure performed in a patient-selected region outside of the United States and the cost of the medical procedure performed within the United States, the medical shared savings unit dividing the savings based on a medical savings plan model when the patient undergoes the medical procedure in the patient-selected region outside of the United States, the medical savings plan model designating less than half of the savings for the patient, the savings including waiving one or more of a co-payment, a deductible, and co-insurance associated with the medical plan.

13. The medical shared savings system in accordance with claim 12, wherein the medical shared savings unit further divides the savings with the patient based on the medical savings plan model.

14. The medical shared savings system in accordance with claim 12, wherein the pricing data includes costs for post-operative services related to the medical procedure.

15. The medical shared savings system in accordance with claim 12, wherein the pricing data includes costs for ongoing prescriptions related to the medical procedure.

16. The medical shared savings system in accordance with claim 12, wherein the one or more computing devices includes a payor computing device associated with a payor of the medical plan and of the savings.

17. The medical shared savings system in accordance with claim 12, wherein the one or more computing devices includes a patient computing device associated with the patient, and configured to receive and transmit the selection to the medical shared savings unit.

* * * * *